United States Patent
Harris et al.

(10) Patent No.: US 11,103,244 B2
(45) Date of Patent: Aug. 31, 2021

(54) SURGICAL STAPLING END EFFECTOR JAW WITH TIP DEFLECTING TOWARD OTHER JAW

(71) Applicant: Ethicon LLC, Guaynabo, PR (US)

(72) Inventors: Jason L. Harris, Lebanon, OH (US); Gregory J. Bakos, Mason, OH (US); Chester O. Baxter, III, Loveland, OH (US); Frederick E. Shelton, IV, Hillsboro, OH (US); Daniel Baber, West Chester, OH (US)

(73) Assignee: Cilag GmbH International, Zug (CH)

( * ) Notice: Subject to any disclaimer, the term of this patent is extended or adjusted under 35 U.S.C. 154(b) by 193 days.

(21) Appl. No.: 16/035,860

(22) Filed: Jul. 16, 2018

(65) Prior Publication Data
US 2018/0325515 A1 Nov. 15, 2018

Related U.S. Application Data

(63) Continuation-in-part of application No. 15/435,573, filed on Feb. 17, 2017, now Pat. No. 10,828,031.

(51) Int. Cl.
*A61B 17/072* (2006.01)
*A61B 17/29* (2006.01)
(Continued)

(52) U.S. Cl.
CPC ...... *A61B 17/072* (2013.01); *A61B 17/07207* (2013.01); *A61B 17/282* (2013.01);
(Continued)

(58) Field of Classification Search
CPC .. A61B 2017/0046; A61B 2017/00964; A61B 2017/07214; A61B 2017/07257;
(Continued)

(56) References Cited

U.S. PATENT DOCUMENTS

| 4,805,823 A | 2/1989 | Rothfuss |
| 5,014,899 A | 5/1991 | Presty et al. |

(Continued)

FOREIGN PATENT DOCUMENTS

| EP | 2772202 | 9/2014 |
| WO | WO 2004/096057 | 11/2004 |

(Continued)

OTHER PUBLICATIONS

European Search Report, Partial, and Written Opinion dated Dec. 9, 2019 for Application No. EP 19186224.2, 11 pgs.
(Continued)

*Primary Examiner* — Chelsea E Stinson
*Assistant Examiner* — Mary C Hibbert-Copeland
(74) *Attorney, Agent, or Firm* — Frost Brown Todd LLC

(57) ABSTRACT

A surgical instrument includes a body, a shaft, and an end effector that is operable to compress, staple, and cut tissue. The end effector includes a pair of jaws. One of the jaws has a greater thickness than the other. On the thicker jaw is a placement tip that is elastically deformable from a biased curved position when the tip is subject to a force, such as the force exerted when tissue is clamped between the jaws. The placement tip extends distally from the distal end of the jaw to which it is attached. The placement tip can have a variety of shapes. The placement tip is made of a material having a lower stiffness than the material of the jaw from which the placement tip extends.

14 Claims, 15 Drawing Sheets

(51) Int. Cl.
*A61B 17/28* (2006.01)
*A61B 17/064* (2006.01)
*A61B 90/00* (2016.01)
*A61B 17/00* (2006.01)

(52) U.S. Cl.
CPC .. *A61B 17/2909* (2013.01); *A61B 2017/0046* (2013.01); *A61B 2017/00964* (2013.01); *A61B 2017/0645* (2013.01); *A61B 2017/07221* (2013.01); *A61B 2017/07257* (2013.01); *A61B 2017/07271* (2013.01); *A61B 2017/07285* (2013.01); *A61B 2017/2913* (2013.01); *A61B 2017/2926* (2013.01); *A61B 2017/2946* (2013.01); *A61B 2090/0807* (2016.02)

(58) Field of Classification Search
CPC .. A61B 2017/07281; A61B 2017/2929; A61B 2017/2946; A61B 2017/320044; A61B 17/072017; A61B 17/072; A61B 2090/0807
USPC .............................. 227/180.1, 19, 151, 152
See application file for complete search history.

(56) References Cited

U.S. PATENT DOCUMENTS

| | | | |
|---|---|---|---|
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,752,965 A | 5/1998 | Francis et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,939,358 B2 | 9/2005 | Palacios et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,066,166 B2 | 11/2011 | Demmy et al. | |
| 8,136,711 B2 | 3/2012 | Beardsley et al. | |
| 8,210,411 B2 | 7/2012 | Yates et al. | |
| 8,348,123 B2 | 1/2013 | Scirica et al. | |
| 8,371,491 B2 | 2/2013 | Huitema et al. | |
| 8,403,195 B2 | 3/2013 | Beardsley et al. | |
| 8,403,196 B2 | 3/2013 | Beardsley et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,496,153 B2 | 7/2013 | Demmy et al. | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,690,039 B2 | 4/2014 | Beardsley et al. | |
| 8,714,429 B2 | 5/2014 | Demmy | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 8,844,790 B2 | 9/2014 | Demmy et al. | |
| 9,016,546 B2 | 4/2015 | Demmy et al. | |
| 9,039,736 B2 | 5/2015 | Scirica et al. | |
| 9,186,142 B2 | 11/2015 | Fanelli et al. | |
| 9,301,759 B2 | 4/2016 | Spivey et al. | |
| 9,433,416 B2 | 9/2016 | Beardsley et al. | |
| 9,517,065 B2 | 12/2016 | Simms et al. | |
| 9,522,004 B2 | 12/2016 | Demmy | |
| 9,597,078 B2 | 3/2017 | Scirica et al. | |
| 9,622,746 B2 | 4/2017 | Simms et al. | |
| 9,713,470 B2 | 7/2017 | Scirica et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,420 B2 | 12/2017 | Shelton, IV et al. | |
| 9,839,421 B2 | 12/2017 | Zerkle et al. | |
| 9,913,642 B2 | 3/2018 | Leimbach et al. | |
| 9,936,952 B2 | 4/2018 | Demmy | |
| 9,936,968 B2 | 4/2018 | Demmy et al. | |
| 9,943,311 B2 | 4/2018 | Scirica et al. | |
| 10,080,564 B2 | 9/2018 | Beardsley et al. | |
| 10,166,023 B2 | 1/2019 | Vendely et al. | |
| 10,349,940 B2 | 7/2019 | Zeiner et al. | |
| 2004/0243151 A1 | 12/2004 | Demmy et al. | |
| 2005/0070929 A1 | 3/2005 | Dalessandro et al. | |
| 2005/0216055 A1 | 9/2005 | Scirica et al. | |
| 2009/0095791 A1 | 4/2009 | Eskaros et al. | |
| 2012/0143218 A1* | 6/2012 | Beardsley .......... A61B 17/1155 606/142 |
| 2012/0289979 A1 | 11/2012 | Eskaros et al. | |
| 2013/0068818 A1 | 3/2013 | Kasvikis | |
| 2013/0334280 A1 | 12/2013 | Krehel et al. | |
| 2014/0166723 A1 | 6/2014 | Beardsley et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239043 A1 | 8/2014 | Simms et al. | |
| 2014/0239044 A1 | 8/2014 | Hoffman | |
| 2015/0173752 A1 | 6/2015 | Demmy et al. | |
| 2015/0272575 A1 | 10/2015 | Leimbach et al. | |
| 2015/0282809 A1 | 10/2015 | Shelton, IV et al. | |
| 2016/0143659 A1 | 5/2016 | Glutz et al. | |
| 2016/0278774 A1 | 9/2016 | Shelton, IV et al. | |
| 2017/0055981 A1 | 3/2017 | Vendely et al. | |
| 2017/0086823 A1 | 3/2017 | Leimbach et al. | |
| 2017/0156725 A1* | 6/2017 | Hemmann ................ A61J 1/00 |
| 2018/0235609 A1 | 8/2018 | Harris et al. | |
| 2018/0235610 A1 | 8/2018 | Harris et al. | |
| 2018/0235611 A1 | 8/2018 | Harris et al. | |
| 2018/0235619 A1 | 8/2018 | Harris et al. | |
| 2018/0325514 A1 | 11/2018 | Harris et al. | |
| 2018/0325516 A1 | 11/2018 | Harris et al. | |
| 2019/0076143 A1* | 3/2019 | Smith ..................... A61B 34/37 |
| 2019/0175173 A1 | 6/2019 | Harris et al. | |

FOREIGN PATENT DOCUMENTS

WO    WO 2013/151888 A1    10/2013
WO    WO 2017/083129          5/2017

OTHER PUBLICATIONS

European Search Report, Extended, and Written Opinion dated Dec. 10, 2019 for Application No. EP 19186231.7, 7 pgs.
European Search Report, Partial, and Provisional Written Opinion dated Oct. 31, 2019 for Application No. EP 119186252.3, 16 pgs.
European Search Report, Extended, and Written Opinion dated Jan. 31, 2020 for Application No. EP 119186252.3, 14 pgs.
International Search Report and Written Opinion dated Dec. 6, 2019 for Application No. PCT/IB2019/055980, 13 pgs.
International Search Report and Written Opinion dated Feb. 27, 2020 for Application No. PCT/IB2019/055983, 20 pgs.
Declaration of Non-Establishment of International Search Report and Written Opinion dated Dec. 13, 2019 for Application PCT/IB2019/055964, 6 pgs.

(56) References Cited

OTHER PUBLICATIONS

European Search Report dated Aug. 7, 2018 for Application No. 18157228.0, 8 pages.
International Search Report and Written Opinion dated Apr. 19, 2018 for International Application No. PCT/US2018/017751, 17 pages.
U.S. Appl. No. 60/466,378, filed Apr. 29, 2003.
U.S. Appl. No. 60/843,254, filed Sep. 8, 2006.
U.S. Appl. No. 11/851,495, filed Sep. 7, 2007.
U.S. Appl. No. 14/868,718, filed Sep. 29, 2015.
U.S. Appl. No. 15/435,573, filed Feb. 17, 2017.
U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
U.S. Appl. No. 16/035,803, filed Jul. 16, 2018.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,856, filed Jul. 16, 2018.
U.S. Appl. No. 16/035,860, filed Jul. 16, 2018.
U.S. Appl. No. 16/035,872, filed Jul. 16, 2018.
U.S. Appl. No. 16/035,893, filed Jul. 16, 2018.
Design U.S. Appl. No. 29/594,332, filed Feb. 17, 2017.
Design U.S. Appl. No. 29/594,335, filed Feb. 17, 2017.
Design U.S. Appl. No. 29/594,340, filed Feb. 17, 2017.
U.S. Appl. No. 15/435,573.
U.S. Appl. No. 16/035,856.
U.S. Appl. No. 16/035,865.
U.S. Appl. No. 16/035,893; and.
U.S. Appl. No. 16/212,868.
European Search Report and Written Opinion dated Nov. 12, 2019 for Application No. EP 19186244.0, 7 pgs.
International Search Report and Written Opinion dated Jan. 2, 2020 for Application No. PCT/IB2019/056041, 11 pgs.

* cited by examiner

SURGICAL STAPLING END EFFECTOR JAW WITH TIP DEFLECTING TOWARD OTHER JAW

PRIORITY

This application is a continuation-in-part of U.S. Non-Provisional patent application Ser. No. 15/435,573, filed Feb. 17, 2017, issued as U.S. Pat. No. 10,828,031 on Nov. 10, 2020, entitled "SURGICAL STAPLER WITH ELASTICALLY DEFORMABLE TIP," the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
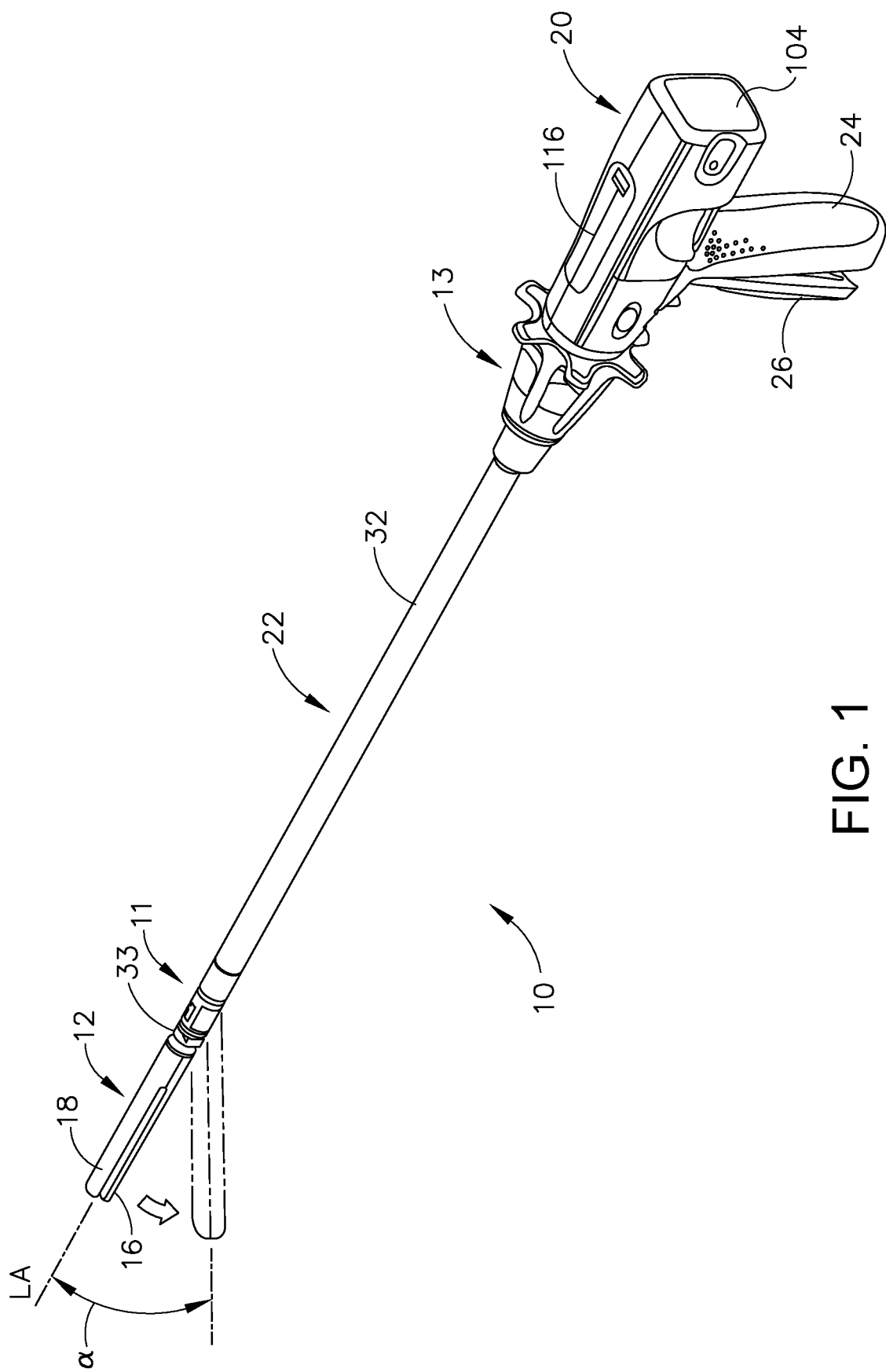
FIG. 1 depicts a perspective view of an exemplary articulating surgical stapling instrument.
Figure 2:
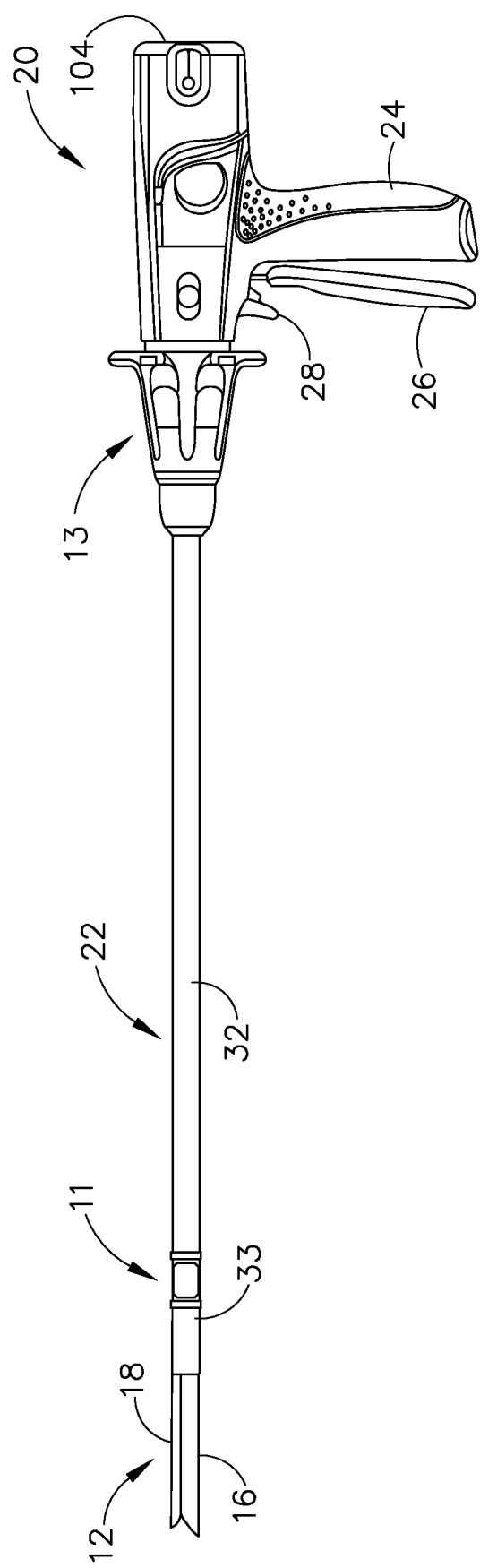
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical," "horizontal," "upper," and "lower" are used herein with respect to the drawings. However, surgical instruments are used in many orientations and positions, and these terms are not intended to be limiting and absolute.

In some versions, shaft (22) is constructed in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pat. No. 9,795,379, entitled "Surgical Instrument with Multi-Diameter Shaft," issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In the present example, anvil (18) can also be considered an upper jaw. Furthermore, in some versions like the present example, the upper jaw or anvil (18) pivots with respect to a stationary lower jaw (16); however, in some other versions the upper jaw or anvil (18) is stationary while the lower jaw (16) pivots. In some versions, lower jaw (16) is constructed in accordance with at least some of the teachings of U.S. Pat. No. 9,808,248, entitled "Installation Features for Surgical Instrument End Effector Cartridge," Nov. 7, 2017, the disclosure of which is incorporated by reference herein. Anvil (18) may be constructed in accordance with at least some of the teachings of U.S. Pat. No. 9,517,065, entitled "Integrated Tissue Positioning and Jaw Alignment Features for Surgical Stapler," published on Dec. 13, 2016, the disclosure of which is incorporated by reference herein; at least some of the teachings of U.S. Pat. No. 9,839,421, entitled "Jaw Closure Feature for End Effector of Surgical Instrument," issued Dec. 12, 2017, the disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," Aug. 1, 2017, the disclosure of which is incorporated by reference herein. Other suitable forms that firing beam (14) may take will be apparent to those of ordinary skill in the art in view of the teachings herein.

Figure 3:
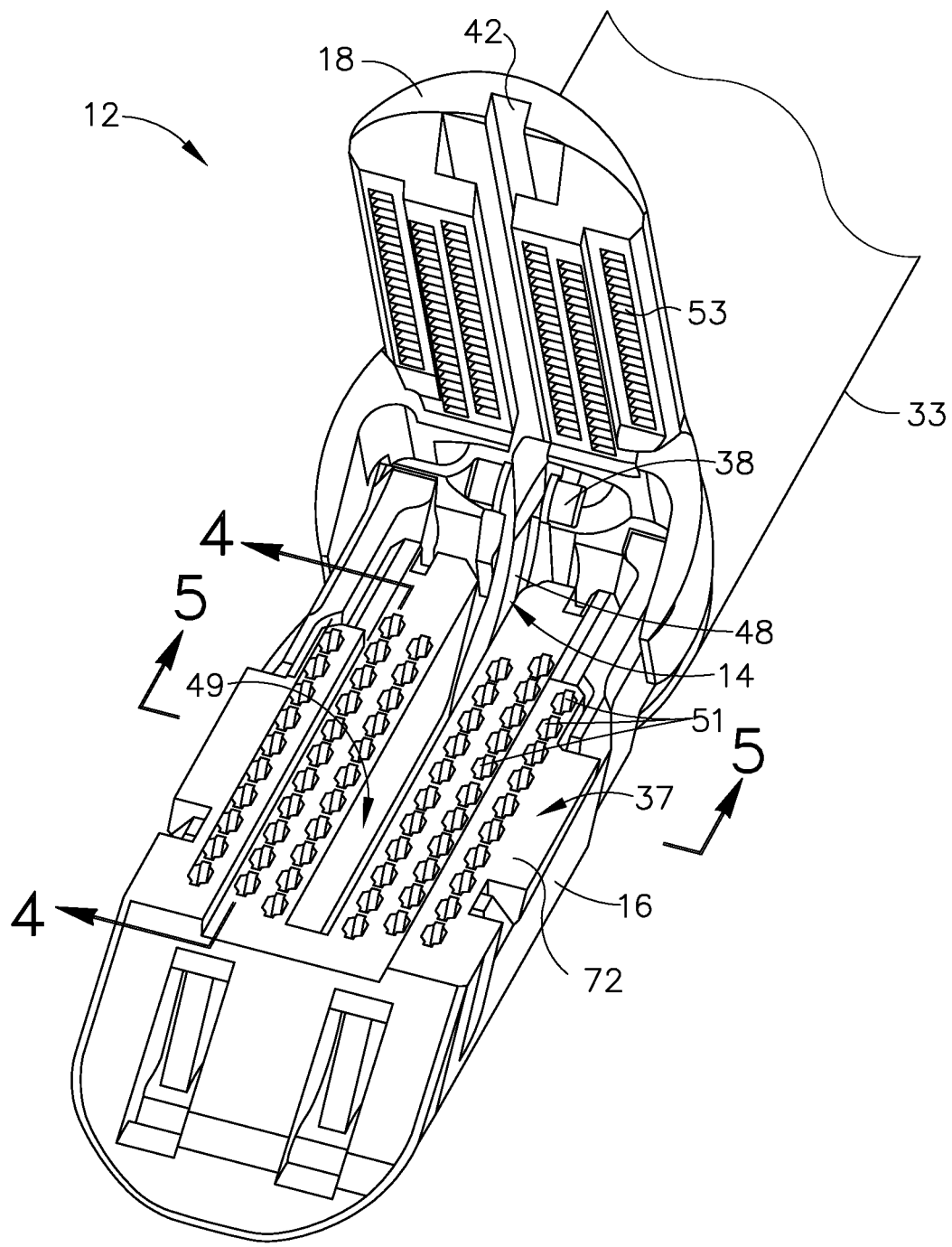
FIG. 3 depicts a perspective view of an opened end effector of the instrument of FIG. 1.
Figure 4A:
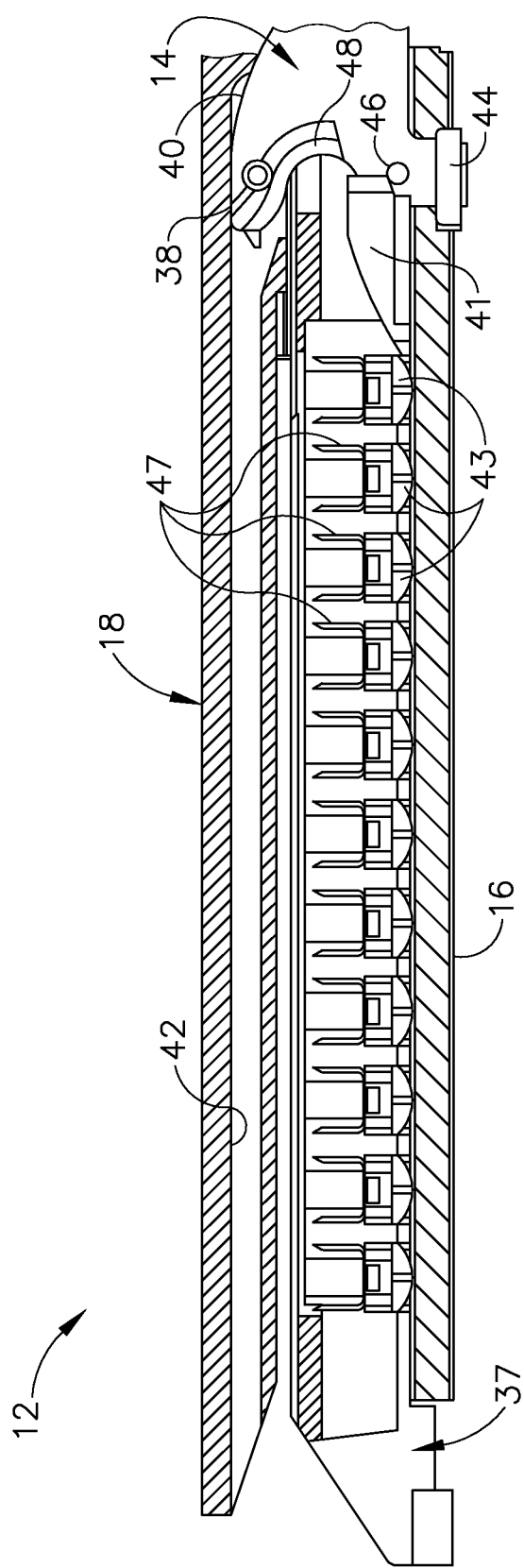
FIG. 4A depicts a side cross-sectional view of the end effector of FIG. 3, taken along line 4-4 of FIG. 3, with the firing beam in a proximal position.
Figure 4B:
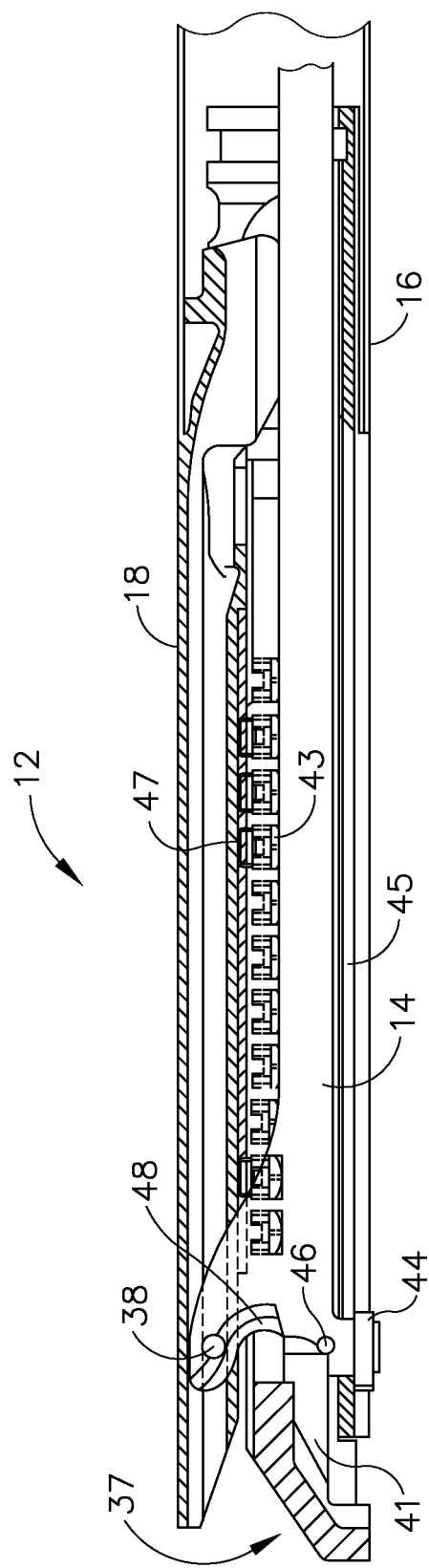
FIG. 4B depicts a side cross-sectional view of the end effector of FIG. 3, taken along line 4-4 of FIG. 3, with the firing beam in a distal position.
Figure 5:
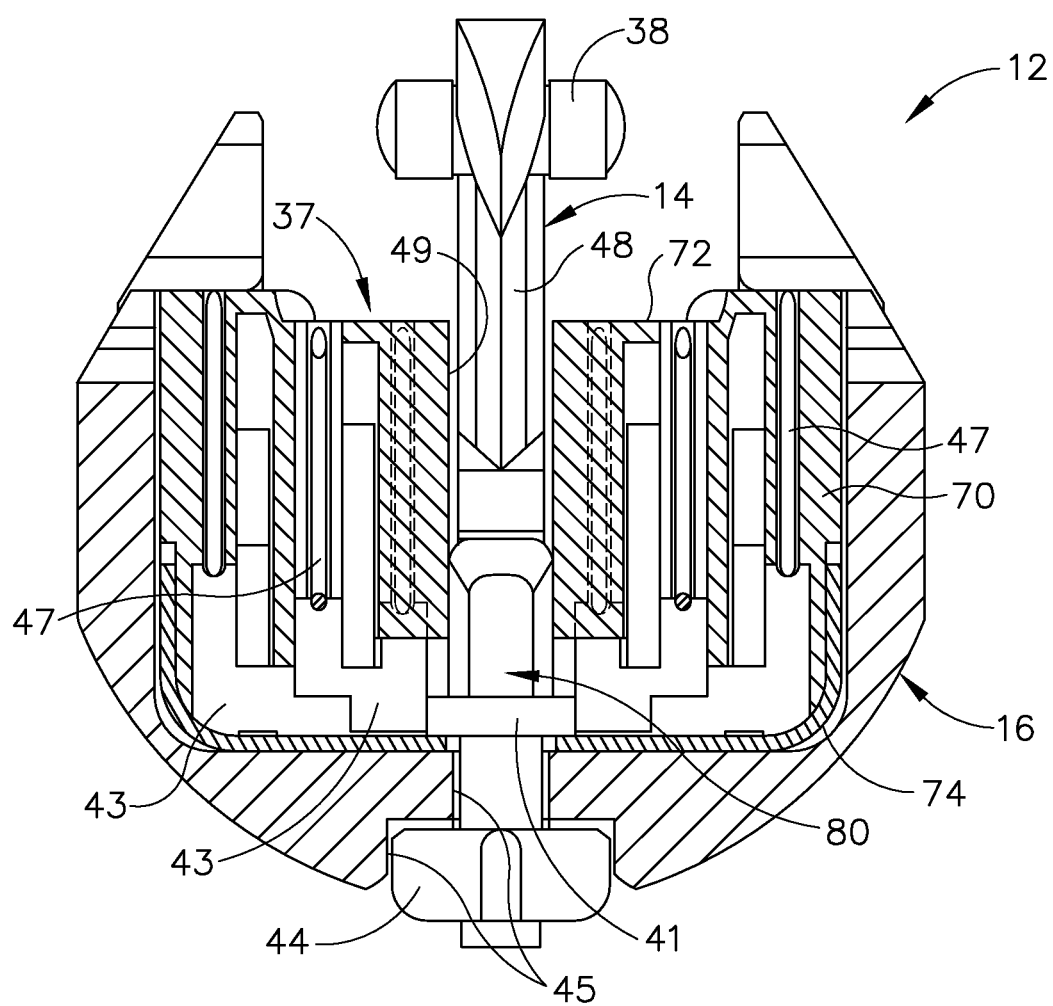
FIG. 5 depicts an end cross-sectional view of the end effector of FIG. 3, taken along line 5-5 of FIG. 3.
Figure 6:
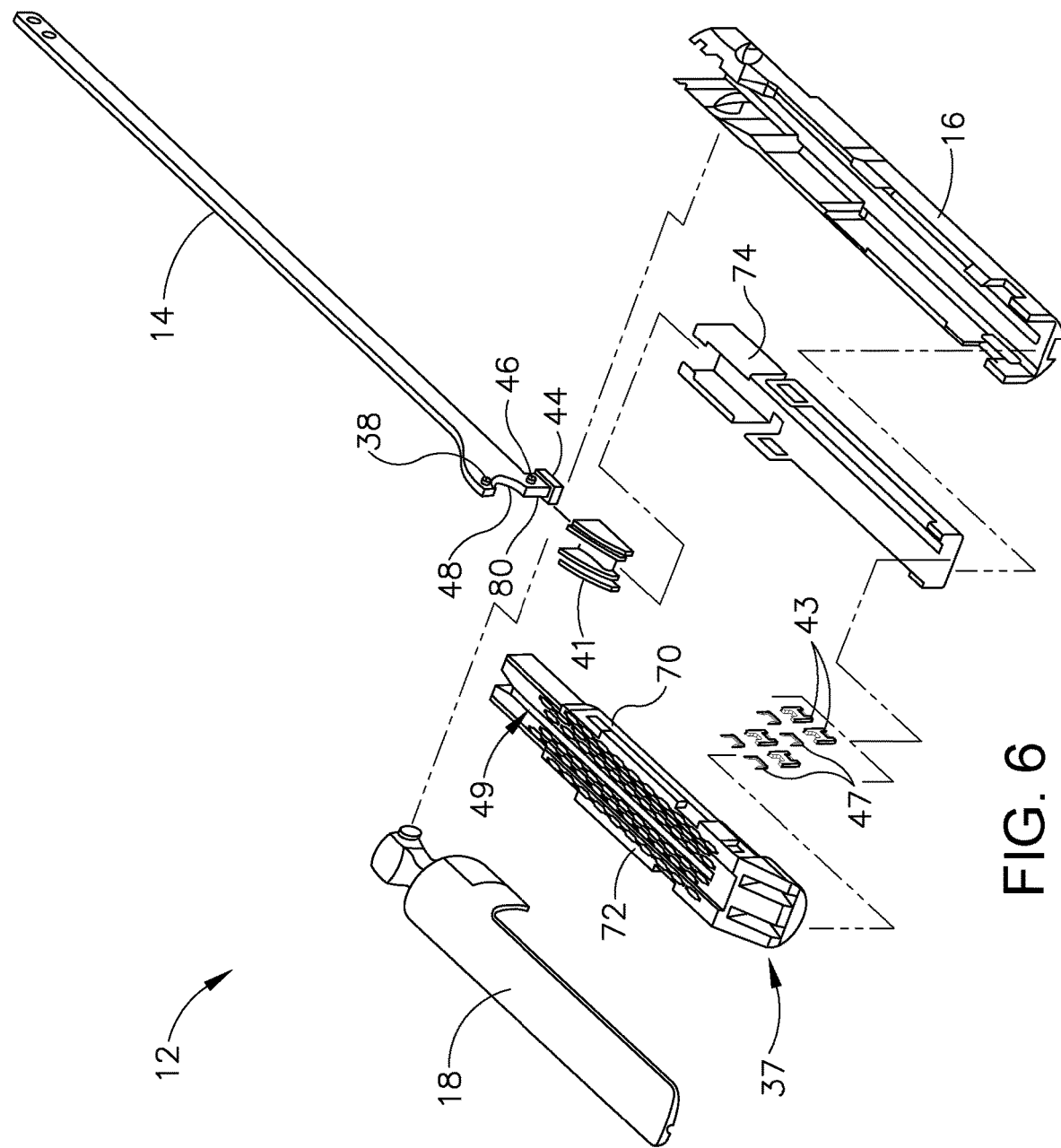
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pat. No. 9,517,065, entitled "Integrated Tissue Positioning and Jaw Alignment Features for Surgical Stapler," published on Dec. 13, 2016, the disclosure of which is incorporated by reference herein. In addition or in the alternative, staple cartridge (37) may be constructed and operable in accordance with at least some of the teachings of U.S. Pat. No. 9,808,248, entitled "Installation Features for Surgical Instrument End Effector Cartridge," Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
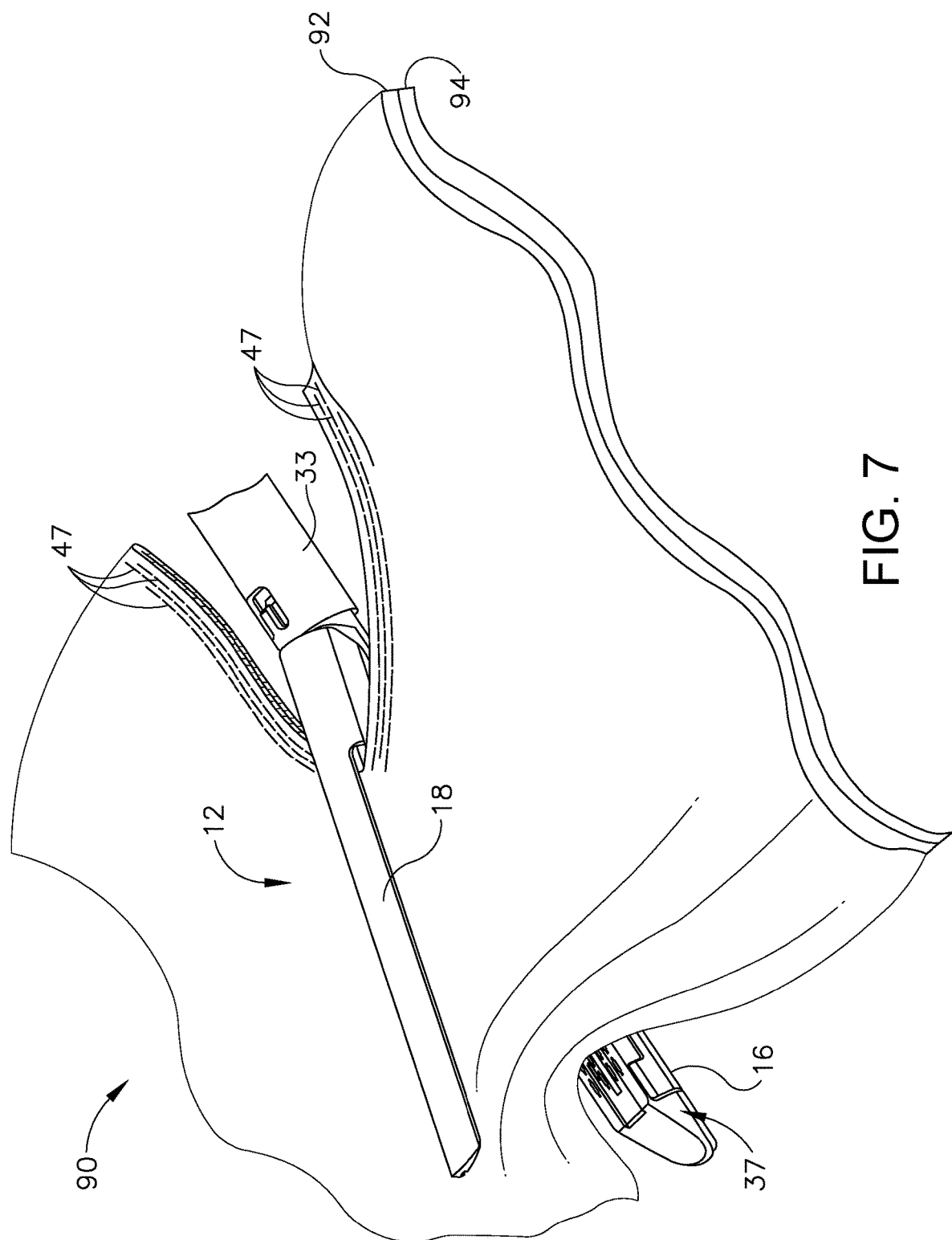
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in U.S. Pat. No. 9,622,746, entitled "Distal Tip Features for End Effector of Surgical Instrument," issued Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pat. No. 8,453,914, the disclosure of which is incorporated by reference herein; and/or in accordance with at least some of the teachings of U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in U.S. Pat. No. 9,622,746, entitled "Distal Tip Features for End Effector of Surgical Instrument," issued Apr. 18, 2017, the disclosure of which is incorporated by reference herein. Additionally, a lockout switch and/or lockout indication and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pat. No. 9,622,746, entitled "Distal Tip Features for End Effector of Surgical Instrument," issued Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; 8,408,439; and/or U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effector with Visualization, Lead-In, and Gathering Feature In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
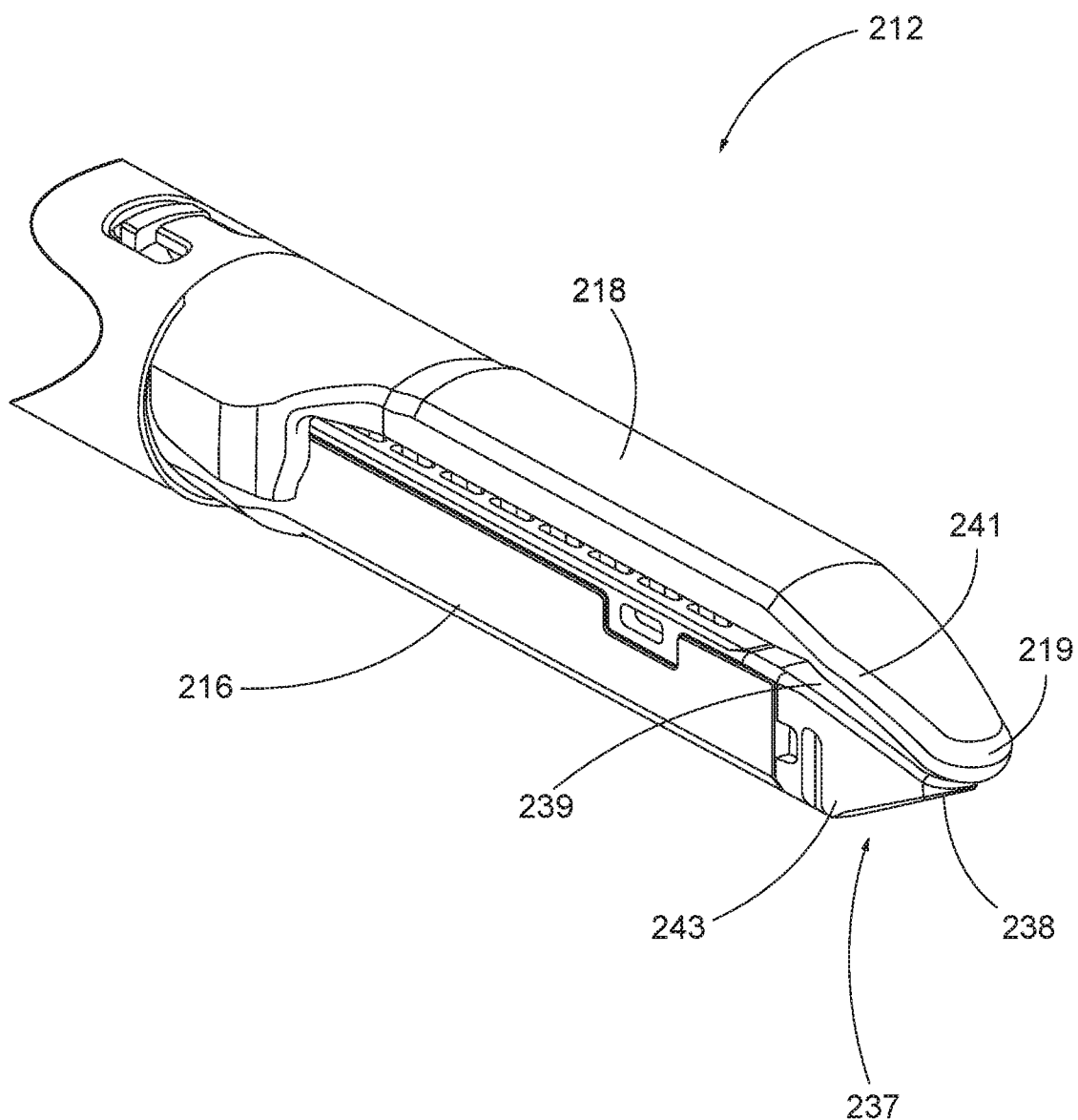
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
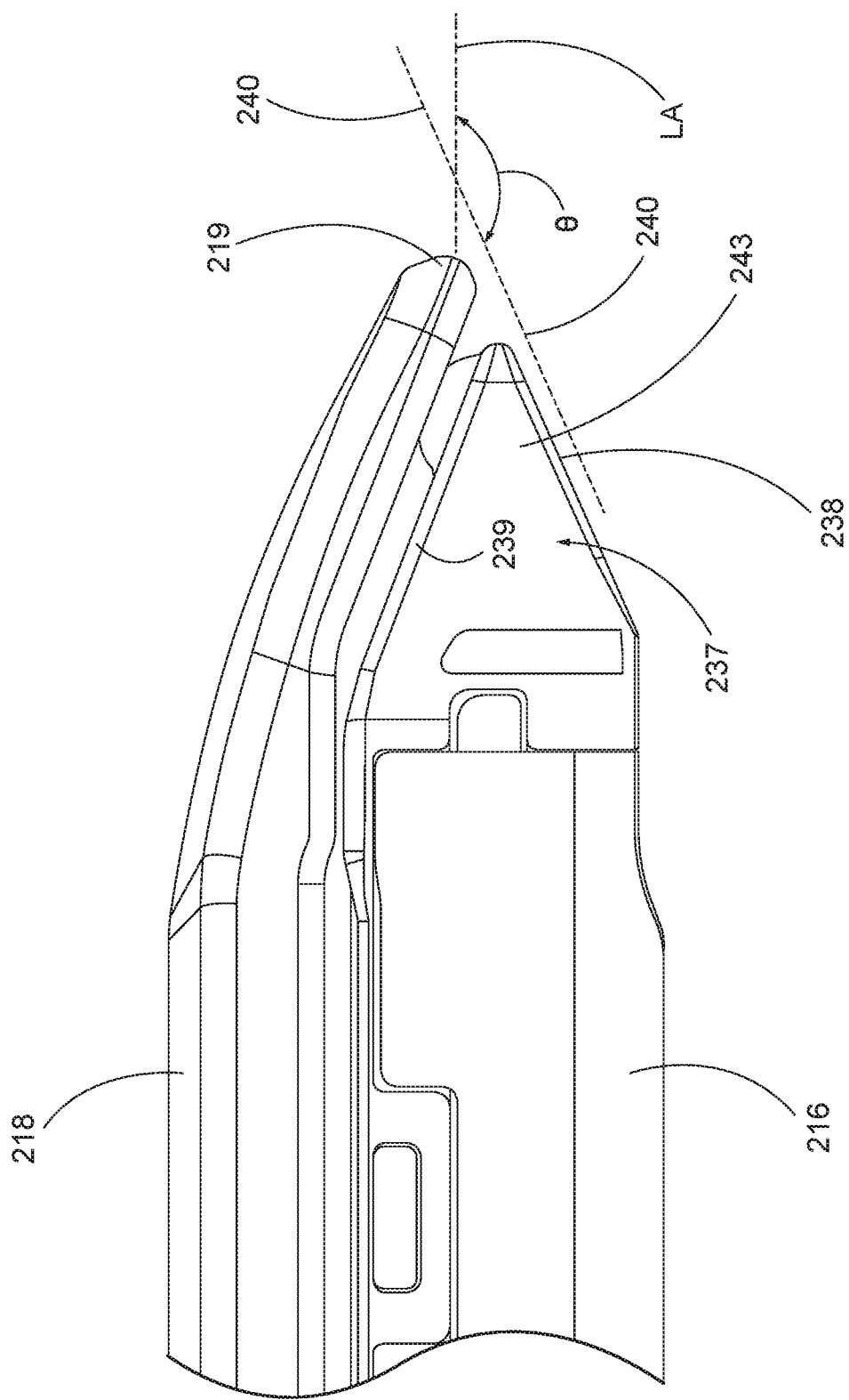
FIG. 9 depicts an enlarged, side view of the end effector of FIG. 8.
Figure 10:
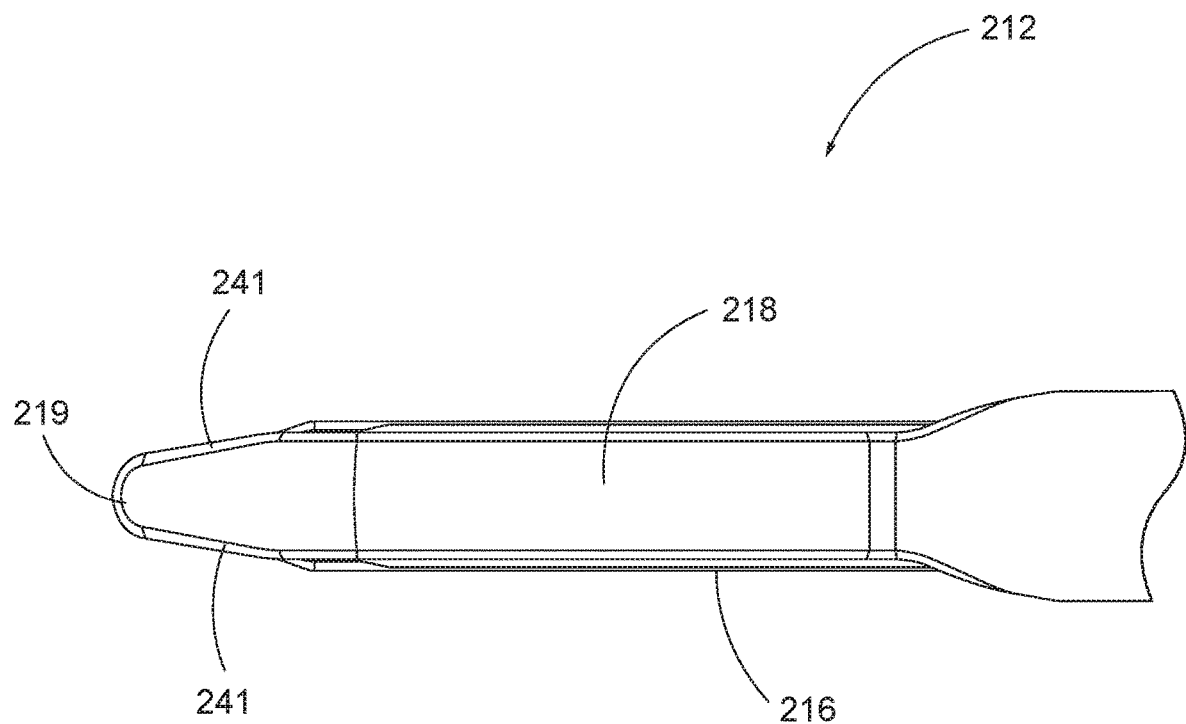
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle ($\theta$).

Viewing angle ($\theta$) may establish the relative visibility that a user has regarding distal tip (219). In particular, the user can see in front of distal tip (219) along any line of sight that passes through the intersection of sight line (240) and longitudinal axis (LA) within viewing angle ($\theta$). For instance, as viewing angle ($\theta$) increases, the user would have greater visibility of the area immediately in front of distal tip (219) from proximal vantage points; whereas as viewing angle ($\theta$) decreases, the user has less visibility of the area in front of distal tip (219) from proximal vantage points. In some versions, viewing angle ($\theta$) defines an angle greater than 90 degrees. Additionally, in some versions, viewing angle ($\theta$) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pat. No. 9,717,497, entitled "Lockout Feature for Movable Cutting Member of Surgical Instrument," Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pat. No. 9,839,421, entitled "Jaw Closure Feature for End Effector of Surgical Instrument," issued Dec. 12, 2017, the disclosure of which is incorporated by reference herein; U.S. Pat. No. 9,622,746, entitled "Distal Tip Features for End Effector of Surgical Instrument," issued Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pat. No. 9,795,379, entitled "Surgical Instrument with Multi-Diameter Shaft," issued Oct. 24, 2017, the disclosure of which is incorporated by reference herein; and/or U.S. Pat. No. 9,808,248, entitled "Installation Features for Surgical Instrument End Effector Cartridge," Nov. 7, 2017, the disclosure of which is incorporated by reference herein. Further modifications that may be incorporated into end effector (212) will be described in greater detail below.

III. End Effectors with Bent or Angled Elastically Deformable Anvil Tips

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
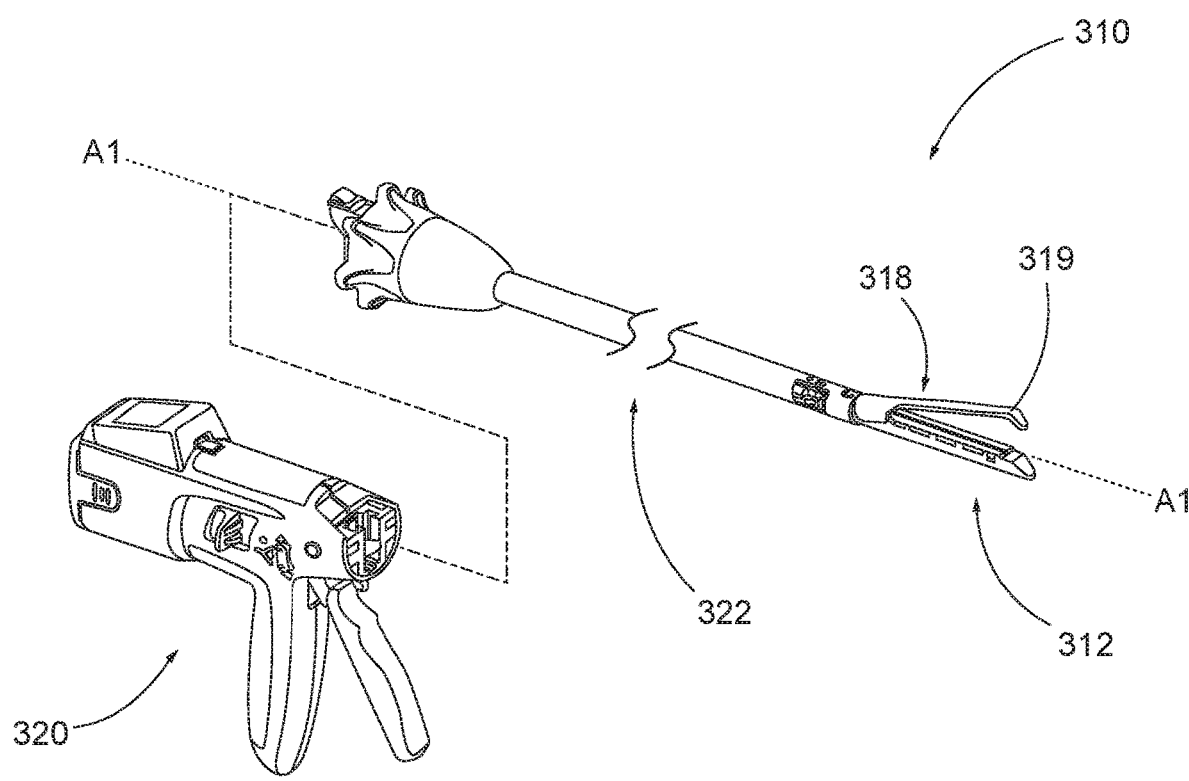
FIG. 11 depicts a perspective view of an exemplary surgical stapling instrument having an end effector with a bent or angled elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. Pub. No. 2017/086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pat. No. 9,913,642, entitled "Surgical Instrument Comprising a Sensor System," issued Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

IV. End Effectors with Elastically Deformable Cartridge Tips

In some instances when a straight and rigid anvil is desired, another approach to modify an end effector for enhanced visualization, maneuverability, and tissue gathering with an atraumatic tip includes the addition of an elastomeric curved tip to the distal end of a cartridge. In this manner, when end effector is closed and maneuvering to a procedure site, the added elastomeric curved tip on the distal end of cartridge fills the space that would otherwise exist at the distal end of the end effector. This configuration can reduce the drag at the distal end when maneuvering the end effector by helping to deflect tissue away from the distal end of end effector when moving the end effector through and along tissue.

Figure 12:
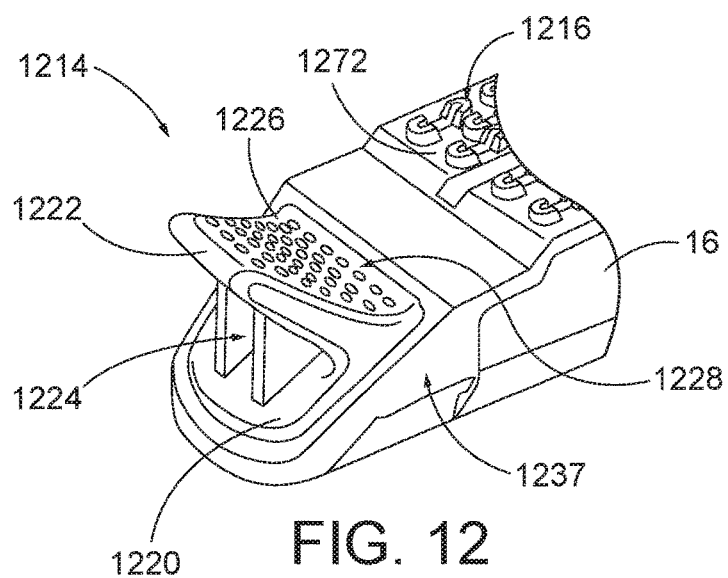
FIG. 12 depicts an enlarged perspective view of a distal portion of an exemplary alternative cartridge for an end effector for use with the surgical stapling instruments described herein.
Figure 13:
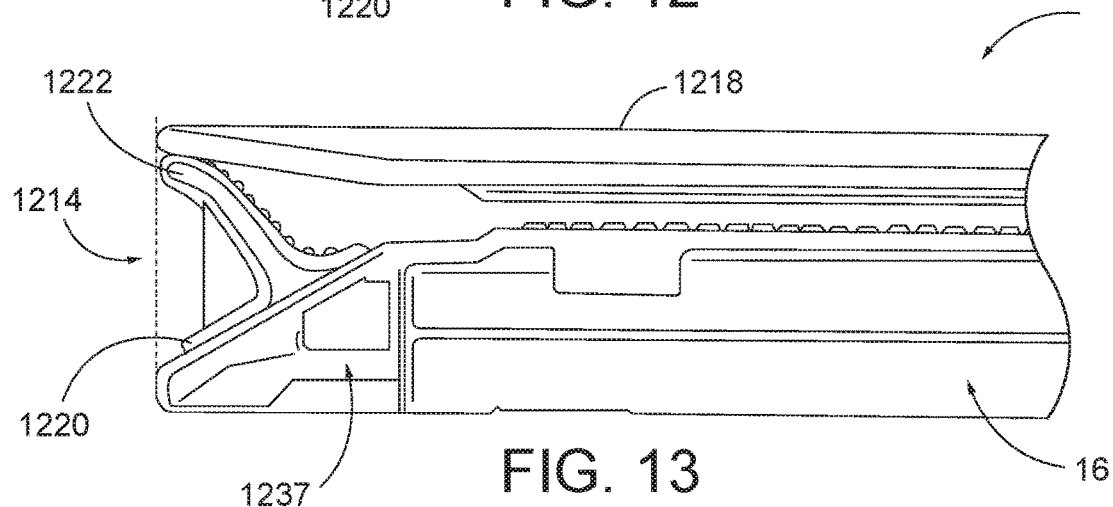
FIG. 13 depicts a side view of a distal portion of an exemplary alternative end effector having the cartridge of FIG. 12, shown without tissue capture.
Figure 14:
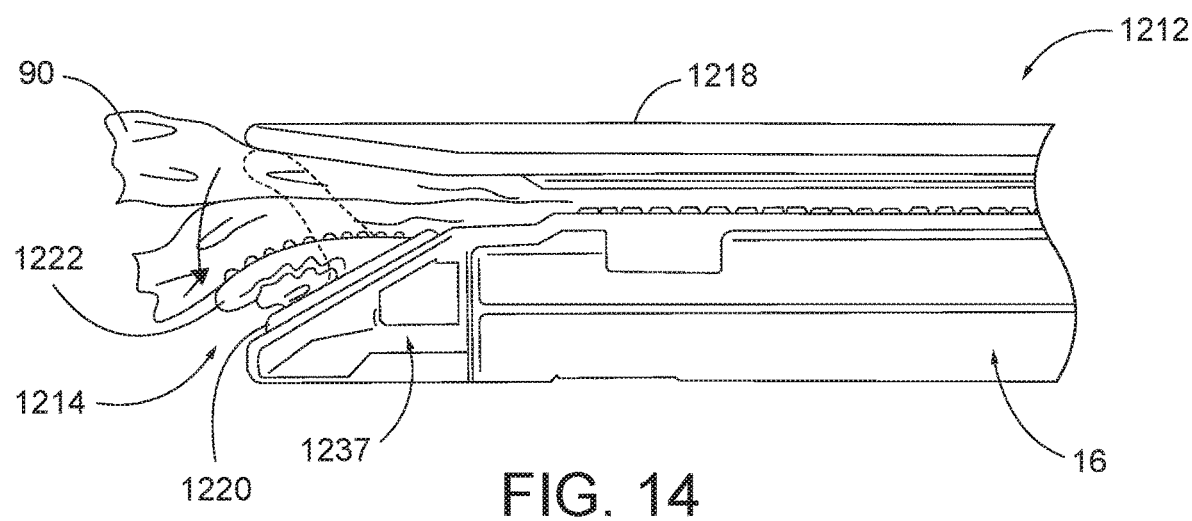
FIG. 14 depicts a side view of a distal portion of the end effector of FIG. 13, shown with tissue captured between the anvil and the cartridge.

FIGS. 12-14 show an exemplary end effector (1212) or components thereof incorporating an elastomeric curved tip (1214) attached to a distal end of a cartridge (1237). In addition to curved tip (1214) and cartridge (1237), end effector (1212) further comprises lower jaw (16) and anvil (1218). Lower jaw (16) is configured to receive cartridge (1237) in the same or similar manner as lower jaw (16) receives cartridge (37) as described above. Anvil (1218) is similar to anvil (18) described above, but with a more pointed distal end similar to anvil (218) but being straight instead of curved. Cartridge (1237) is similar to cartridge (37) as described above with a difference being the incorporation of elastomeric curved tip (1214). As shown in FIG. 12, cartridge (1237) further comprises tissue gripping features (1216) located on an upper deck (1272) of cartridge (1237). Such tissue gripping features (1216) are optional features and they may be omitted in other versions.

As mentioned above, elastomeric curved tip (1214) is attached with the angled distal end of cartridge (1237). The connection of curved tip (1214) to cartridge (1237) may be achieved using a chemical or mechanical fastening. In view of the teachings herein those of ordinary skill in the art will appreciate the various ways to connect curved tip (1214) with distal end of cartridge (1237). In some versions, curved tip (1214) is bonded to cartridge (1237) using a molding process. In such examples, distal end of cartridge (1237) may comprise various structural features configured to engage with elastomeric material of curved tip (1214) during molding to thereby secure curved tip (1214) to distal end of cartridge (1237). In the present example, curved tip (1214) is resiliently biased to extend substantially perpendicularly from the angled distal face of cartridge (1237), though it should be understood that curved tip (1214) may have any other suitable angular relationship with the angled distal face of cartridge (1237). In addition, curved tip (1214) is resiliently biased to extend along a plane that is oriented obliquely relative to the longitudinal axis of end effector (1212) in the present example.

Curved tip (1214) comprises lower lip (1220), upper lip (1222), and dividers (1224). Lower lip (1220) attaches with the angled distal end of cartridge (1237) as described above. Upper lip (1222) extends from and connects with a proximal portion of lower lip (1220). Dividers (1224) extend vertically from lower lip (1220) and connect lower lip (1220) and upper lip (1222). In the present example, upper lip (1222) comprises top surface (1226) that includes gripping features (1228) configured to improve gripping tissue clamped between anvil (1218) and cartridge (1237), for example as shown in FIG. 14.

Referring to FIGS. 13 and 14, end effector (1212) is shown in the closed position both when not clamping tissue and when clamping tissue. As shown, in the closed position in either scenario, the distal end of anvil (1218) aligns with the longitudinal position of the distal end of cartridge (1237). In other versions, end effector (1212) may be configured such that the distal end of anvil (1218) extends past cartridge (1237) when end effector (1212) is closed. Still in other versions, end effector (1212) may be configured such that the distal end of anvil (1218) terminates proximal to the distal end of cartridge (1237) when end effector (1212) is closed.

As shown in FIG. 14, when tissue (90) is captured between anvil (1218) and cartridge (1237), elastomeric curved tip (1214) deforms from its open state in FIG. 13 to a closed state as shown in FIG. 14. In this deformed state, upper lip (1222) deflects downwardly toward lower lip (1220). Furthermore, dividers (1224) are compressed and deflect laterally. As shown in FIG. 14, in its deformed state, upper lip (1222) of curved tip (1214) extends distally of anvil (1218) and cartridge (1237). With tissue clamped between end effector (1212) a cutting and stapling sequence can now occur with end effector (1212) in a similar manner to that described above with respect to end effector (12). When the clamping force is released, curved tip (1214) may resiliently return to the configuration and orientation shown in FIGS. 12-13.

In view of the teachings herein, it will be appreciated that end effector (1212) may be used in place of any of the other end effectors described herein. For instance, end effector (1212) may be used in place of end effector (12) shown in FIG. 1, or in place of end effector (312) shown in FIG. 11. In some versions, end effector (1212) may be integrally formed with either shaft (22, 322) or alternatively may be separately formed and then combined. In some versions, end effector (1212) may be provided for use in robotic systems as described above.

V. End Effectors with Elastically Deformable Tips on Thicker Jaw

In some instances when a straight and rigid jaw is desired, another approach to modify an end effector for enhanced visualization, maneuverability, and tissue gathering includes the addition of a placement tip on the distal end of the opposing jaw. In this manner, when end effector is closed and maneuvering to a procedure site, the placement tip fills at least some of the space that would otherwise exist at the distal end of the end effector. This configuration can reduce the drag at the distal end when maneuvering the end effector by helping to deflect tissue away from the distal end of end effector when moving the end effector through and along tissue. In some cases as will be described, the placement tip is made of a elastically deformable material such that the placement tip is responsive or deflects when subject to force associated with clamping tissue between the jaws.

Figure 15:
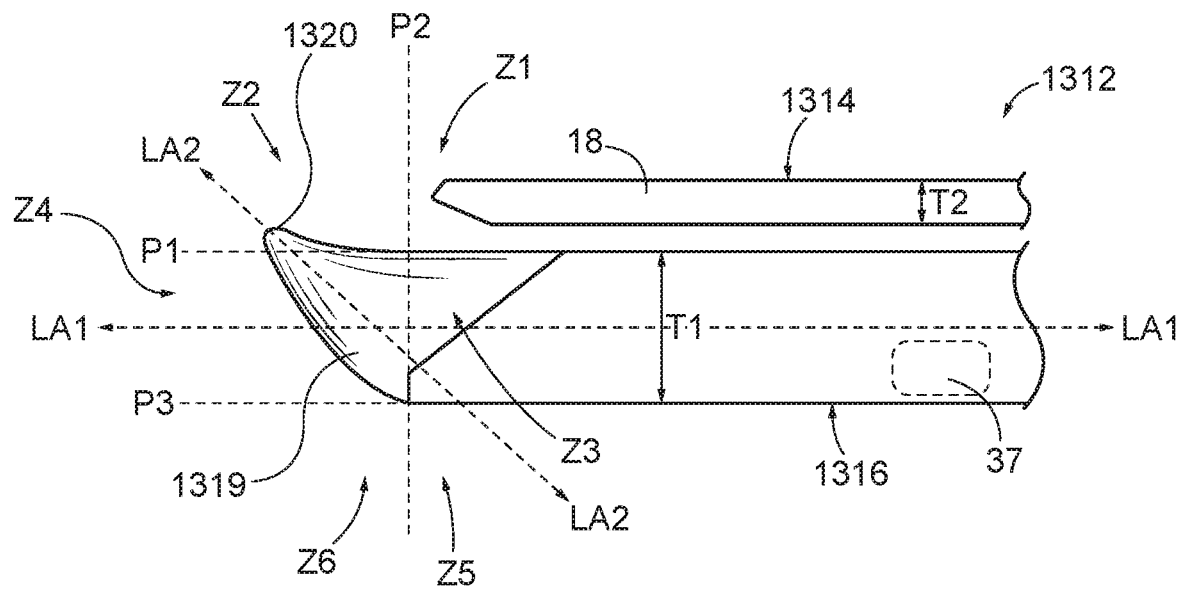
FIG. 15 depicts an enlarged side view of a distal portion of another exemplary end effector for use with the surgical stapling instruments described herein, showing a deformable tip extending from a thicker jaw.

FIG. 15 shows an enlarged view of end effector (1312), which is configured for use with instruments (10, 310) and/or for robotic use as described above. End effector (1312) comprises jaw (1314) and jaw (1316) that are configured in an opposing manner. Furthermore, jaws (1314, 1316) are operably configured such that one or both of the jaws (1314, 1316) are movable relative to the other to change the state of end effector (1312) from an open position or state to a closed position or state. For instance, this opening and closing of end effector (1312) provides for the ability to grasp, clamp, or release tissue. In the present example, FIG. 15 shows jaw (1314) as an upper jaw and jaw (1316) as a lower jaw. As mentioned above, the terms "upper" and "lower" are used as relative spatial references to help clarify the description of end effector (1312) and should not be interpreted in a limiting manner.

In the present example, a distal tip or placement tip (1319) extends distally from jaw (1316). Jaw (1316), excluding placement tip (1319), defines a longitudinal axis (LA1) that generally extends along the length of jaw (1316) from the proximal end to the distal end. Placement tip (1319) defines another longitudinal axis (LA2). In the present example, axis (LA2) defined by placement tip (1319) extends in a non-parallel manner with respect to longitudinal axis (LA1) defined by jaw (1316) from which placement tip (1319) extends. With this configuration, placement tip (1319) extends from jaw (1316) toward opposing jaw (1314). In other words, longitudinal axis (LA2) extends away from longitudinal axis (LA1) toward jaw (1314).

As shown in FIG. 15, jaw (1316) comprises a thickness (T1), while jaw (1314) comprises a thickness (T2). In the illustrated examples, jaw (1316) has a greater thickness than jaw (1314). Furthermore, placement tip (1319) connects with and extends from thicker jaw (1316) in the present example. As mentioned above in the present example placement tip (1316) extends from thicker jaw (1316) toward opposing thinner jaw (1314). As also shown in the illustrated version of FIG. 15, but not required in all versions, placement tip (1319) comprises about the same thickness as jaw (1316) to which it connects, at its thickest point. Furthermore, placement tip (1319) bends or curves toward jaw (1314) such that placement tip (1319) comprises a taper. In the present example placement tip (1319) tapers longitudinally. In some versions, placement tip (1319) tapers laterally. Still in some other versions, placement tip (1319) tapers both longitudinally and laterally. In view of the teachings herein, other configurations for the taper of placement tip (1319), or lack thereof, will be apparent to those of ordinary skill in the art.

In some versions of end effector (1312), placement tip (1319) is constructed of an elastically deformable material. In this manner placement tip (1319) is biased to an initial orientation or position when not subjected to force, and placement tip (1319) deflects to another orientation or position when subject to force, i.e. the force exerted on placement tip (1319) when clamping tissue. When the force is removed, placement tip (1319) is resilient and thus returns to its initial orientation or position. Additionally, in the present example, placement tip (1319) is constructed of a resilient material as mentioned, where that material and placement tip (1319) has a lower stiffness than jaw (1316) to which placement tip (1319) connects. In other words, the material of placement tip (1319) has a lower stiffness than the material of jaw (1316) from which placement tip (1319) extends. In some instances, placement tip (1319) tapers such that placement tip (1319) comprises a distal end (1320) that is pointed. In such instances, where placement tip (1319) is comprised of an elastomeric and deflectable material, placement tip (1319) is still configured as an atraumatic tip despite its pointed shape.

As described further above, end effector (1312) like end effectors (1212, 212), is configured such that one of jaws (1314, 1316) comprise anvil (18), while the other of jaws (1314, 1316) comprise cartridge (37). Although not required in all versions, in the present example jaw (1316) is configured to selectively retain cartridge (37) or a similar cartridge, and jaw (1314) comprises anvil (18) or a similar anvil. With this configuration, the thicker jaw (1316) comprises cartridge (37) as well as placement tip (1319). In some other versions, the thicker jaw with placement tip (1319) may be configured as anvil (18), while the thinner jaw may be configured to selectively retain the cartridge (37). Thus it is not required in all versions that the thicker jaw necessarily is the jaw that also selectively retains the cartridge. Furthermore, while the present example illustrates jaw (1316), to which placement tip (1319) connects, as a lower jaw relative to jaw (1314), in other versions the thicker jaw having placement tip (1319) is an upper jaw that may or may not also include cartridge (37) as mentioned above. In view of the teachings herein, other ways to configure end effector (1312) with placement tip (1319) on the thicker jaw will be apparent to those of ordinary skill in the art.

Figure 16:
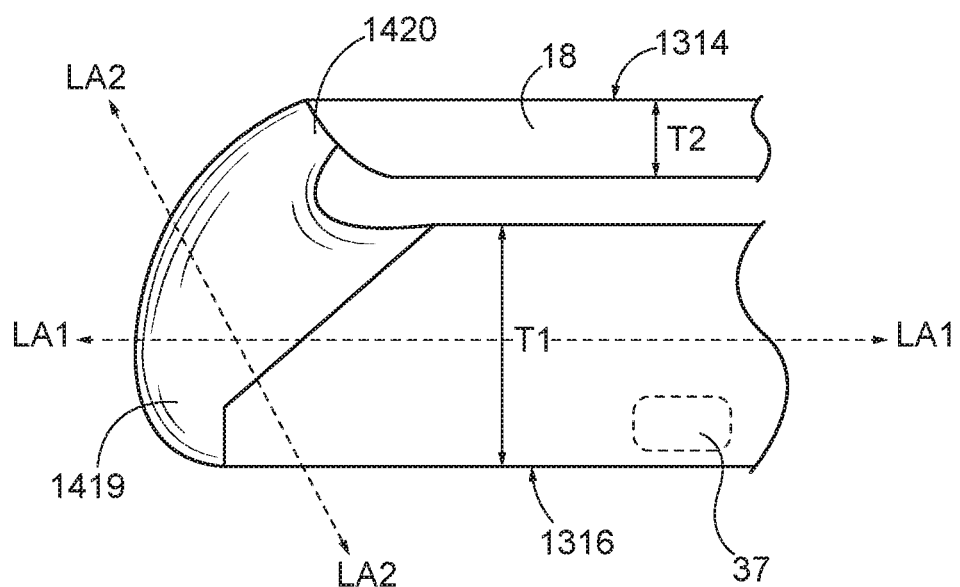
FIG. 16 depicts an enlarged side view of a distal portion of another exemplary end effector for use with the surgical stapling instruments described herein, showing a deformable tip extending from a thicker jaw in a touching or contacting configuration with the opposite jaw.
Figure 17:
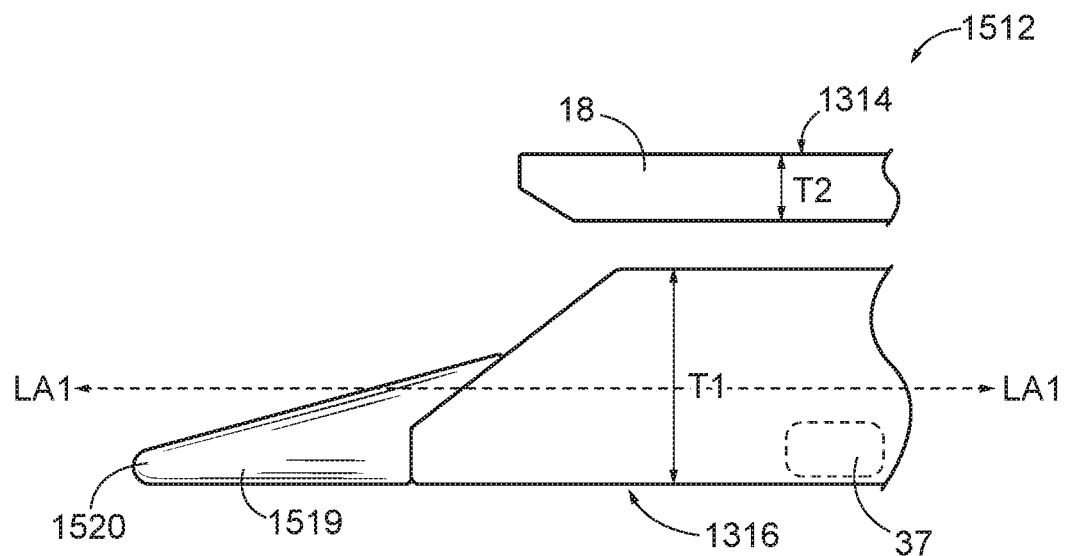
FIG. 17 depicts an enlarged side view of a distal portion of another exemplary end effector for use with the surgical stapling instruments described herein, showing a deformable tip extending from a thicker jaw in a straight configuration.
Figure 18:
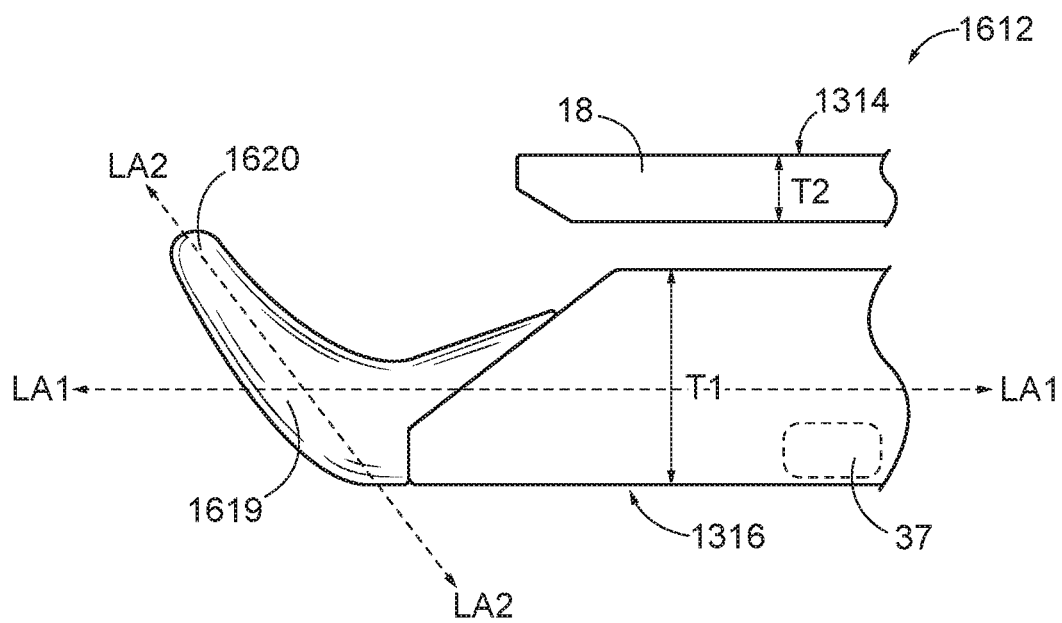
FIG. 18 depicts an enlarged side view of a distal portion of another exemplary end effector for use with the surgical stapling instruments described herein, showing a deformable tip extending from a thicker jaw in a curved non-touching or non-contacting configuration with the opposite jaw.

FIGS. 16-18 illustrate other enlarged views of exemplary end effectors suitable for use with instruments (10, 310) and/or for robotic use as described above. Other than the placement tips, the other components of the end effectors of FIGS. 16-18 are the same as those of end effector (1312) of FIG. 15. Therefore, the discussion that follows focuses on the placement tips rather than repeating the description of those features that are the same as with end effector (1312) and already described above.

FIG. 16 shows an enlarged view of an end effector (1412). End effector (1412) is the same as end effector (1312) with the exception that placement tip (1319) is replaced with placement tip (1419). Placement tip (1419) extends from jaw (1316), which is the thicker jaw compared to jaw (1314) as described above. In the version shown in FIG. 16, placement tip (1419) curves or bends away from jaw (1316) and longitudinal axis (LA1) and toward jaw (1314). In the present example, placement tip (1419) comprises an end (1420) that touches or contacts the distal-most end of jaw (1314) when end effector is in a closed an unloaded state where tissue is not between jaws (1314, 1316). With this configuration, placement tip (1419) fills the gap or space between jaws (1314, 1316) when end effector (1412) is closed. Such a configuration can improve maneuverability when moving end effector (1412) through tissue to a desired site.

As also shown in the illustrated version of FIG. 16, but not required in all versions, placement tip (1419) comprises about the same thickness as jaw (1316) to which it connects, at its thickest point. Furthermore, placement tip (1419) comprises a taper such that placement tip (1419) tapers as it extends away from jaw (1316) and toward jaw (1314). In the present example placement tip (1419) tapers longitudinally. In some versions, placement tip (1419) tapers laterally. Still in some other versions, placement tip (1419) tapers both longitudinally and laterally. In view of the teachings herein, other configurations for the taper of placement tip (1419), or lack thereof, will be apparent to those of ordinary skill in the art.

In the present example, but not required in all examples, placement tip (1419) is constructed of an elastically deformable material. In this manner placement tip (1419) is biased to an initial orientation or position when not subjected to force, and placement tip (1419) deflects to another orientation or position when subject to force, i.e. the force exerted on placement tip (1419) when clamping tissue. When the force is removed, placement tip (1419) is resilient and thus returns to its initial orientation or position. Additionally, in the present example, placement tip (1419) is constructed of a resilient material as mentioned, where that material and placement tip (1419) has a lower stiffness than jaw (1316) to which placement tip (1419) connects. In other words, the material of placement tip (1419) has a lower stiffness than the material of jaw (1316) from which placement tip (1419) extends. In some instances, placement tip (1419) tapers such that placement tip (1419) comprises a distal end (1420) that is pointed. In such instances, where placement tip (1419) is comprised of an elastomeric and deflectable material, placement tip (1419) is still configured as an atraumatic tip despite its pointed shape.

End effector (1412), like end effector (1312) and others described above, is configured such that one of jaws (1314, 1316) comprise anvil (18), while the other of jaws (1314, 1316) comprise cartridge (37). Although not required in all versions, in the present example jaw (1316) is configured to selectively retain cartridge (37) or a similar cartridge, and jaw (1314) comprises anvil (18) or a similar anvil. With this configuration, the thicker jaw (1316) comprises cartridge (37) as well as placement tip (1419). In some other versions, the thicker jaw with placement tip (1419) may be configured as anvil (18), while the thinner jaw may be configured to selectively retain the cartridge (37). Thus, it is not required in all versions that the thicker jaw necessarily is the jaw that also selectively retains the cartridge. Furthermore, while the present example illustrates jaw (1316), to which placement tip (1419) connects, as a lower jaw relative to jaw (1314), in other versions the thicker jaw having placement tip (1419) is an upper jaw that may or may not also include cartridge (37) as mentioned above. In view of the teachings herein, other ways to configure end effector (1412) with placement tip (1419) on the thicker jaw will be apparent to those of ordinary skill in the art.

FIG. 17 shows an enlarged view of an end effector (1512). End effector (1512) is the same as end effector (1312) with the exception that placement tip (1319) is replaced with placement tip (1519). Placement tip (1519) extends from jaw (1316), which is the thicker jaw compared to jaw (1314) as described above. In the version shown in FIG. 17, placement tip (1519) comprises a straight geometry where placement tip (1519) extends distally from jaw (1316) in a straight fashion without bending or curving toward opposing jaw (1314). This configuration provides a large gap or space between jaws (1314, 1316) when end effector (1512) is in a closed and unloaded state as shown in FIG. 17. Such a configuration can improve tissue capture and visibility when clamping, cutting, and stapling tissue.

As also shown in the illustrated version of FIG. 17, but not required in all versions, placement tip (1519) is less thick compared to thickness (T1) of jaw (1316) to which placement tip (1519) connects. Furthermore, placement tip (1519) comprises a taper such that placement tip (1519) tapers as it extends away from jaw (1316). In the present example placement tip (1519) tapers longitudinally. In some versions, placement tip (1519) tapers laterally. Still in some other versions, placement tip (1519) tapers both longitudinally and laterally. In view of the teachings herein, other configurations for the taper of placement tip (1519), or lack thereof, will be apparent to those of ordinary skill in the art.

In the present example, but not required in all examples, placement tip (1519) is constructed of an elastically deformable material. In this manner placement tip (1519) is biased to an initial orientation or position when not subjected to force, and placement tip (1519) deflects to another orientation or position when subject to force, i.e. the force exerted on placement tip (1519) when clamping tissue. When the force is removed, placement tip (1519) is resilient and thus returns to its initial orientation or position. Additionally, in the present example, placement tip (1519) is constructed of a resilient material as mentioned, where that material and placement tip (1519) has a lower stiffness than jaw (1316) to which placement tip (1519) connects. In other words, the material of placement tip (1519) has a lower stiffness than the material of jaw (1316) from which placement tip (1519) extends. In some instances, placement tip (1519) tapers such that placement tip (1519) comprises a distal end (1520) that is pointed. In such instances, where placement tip (1519) is comprised of an elastomeric and deflectable material, placement tip (1519) is still configured as an atraumatic tip despite its pointed shape.

End effector (1512), like end effector (1312) and others described above, is configured such that one of jaws (1314, 1316) comprise anvil (18), while the other of jaws (1314, 1316) comprise cartridge (37). Although not required in all versions, in the present example jaw (1316) is configured to selectively retain cartridge (37) or a similar cartridge, and jaw (1314) comprises anvil (18) or a similar anvil. With this configuration, the thicker jaw (1316) comprises cartridge (37) as well as placement tip (1519). In some other versions, the thicker jaw with placement tip (1519) may be configured as anvil (18), while the thinner jaw may be configured to selectively retain the cartridge (37). Thus, it is not required in all versions that the thicker jaw necessarily is the jaw that also selectively retains the cartridge. Furthermore, while the present example illustrates jaw (1316), to which placement tip (1519) connects, as a lower jaw relative to jaw (1314), in other versions the thicker jaw having placement tip (1519) is an upper jaw that may or may not also include cartridge (37) as mentioned above. In view of the teachings herein, other ways to configure end effector (1512) with placement tip (1519) on the thicker jaw will be apparent to those of ordinary skill in the art.

FIG. 18 shows an enlarged view of an end effector (1612). End effector (1612) is the same as end effector (1312) with the exception that placement tip (1319) is replaced with placement tip (1619). Placement tip (1619) extends from jaw (1316), which is the thicker jaw compared to jaw (1314) as described above. In the version shown in FIG. 18, placement tip (1619) curves or bends away from jaw (1316) and longitudinal axis (LA1) and toward jaw (1314). In the present example, placement tip (1619) comprises an end (1620) that does not touch or contact the distal-most end of jaw (1314) when end effector is in a closed an unloaded state where tissue is not between jaws (1314, 1316). With this configuration, there remains a gap or space between jaws (1314, 1316) when end effector (1612) is closed and in an unloaded state as shown in FIG. 18. Such a configuration can improve tissue capture and visibility when clamping, cutting, and stapling tissue.

As also shown in the illustrated version of FIG. 18, but not required in all versions, placement tip (1619) is less thick compared to thickness (T1) of jaw (1316) to which placement tip (1619) connects. Furthermore, placement tip (1619) comprises a taper such that placement tip (1619) tapers as it extends away from jaw (1316). In the present example placement tip (1619) tapers longitudinally. In some versions, placement tip (1619) tapers laterally. Still in some other versions, placement tip (1619) tapers both longitudinally and laterally. In view of the teachings herein, other configurations for the taper of placement tip (1619), or lack thereof, will be apparent to those of ordinary skill in the art.

In the present example, but not required in all examples, placement tip (1619) is constructed of an elastically deformable material. In this manner placement tip (1619) is biased to an initial orientation or position when not subjected to force, and placement tip (1619) deflects to another orientation or position when subject to force, i.e. the force exerted on placement tip (1619) when clamping tissue. When the force is removed, placement tip (1619) is resilient and thus returns to its initial orientation or position. Additionally, in the present example, placement tip (1619) is constructed of a resilient material as mentioned, where that material and placement tip (1619) has a lower stiffness than jaw (1316) to which placement tip (1619) connects. In other words, the material of placement tip (1619) has a lower stiffness than the material of jaw (1316) from which placement tip (1619) extends. In some instances, placement tip (1619) tapers such that placement tip (1619) comprises a distal end (1620) that is pointed. In such instances, where placement tip (1619) is comprised of an elastomeric and deflectable material, placement tip (1619) is still configured as an atraumatic tip despite its pointed shape.

End effector (1612), like end effector (1312) and others described above, is configured such that one of jaws (1314, 1316) comprise anvil (18), while the other of jaws (1314, 1316) comprise cartridge (37). Although not required in all versions, in the present example jaw (1316) is configured to selectively retain cartridge (37) or a similar cartridge, and jaw (1314) comprises anvil (18) or a similar anvil. With this configuration, the thicker jaw (1316) comprises cartridge (37) as well as placement tip (1619). In some other versions, the thicker jaw with placement tip (1619) may be configured as anvil (18), while the thinner jaw may be configured to selectively retain the cartridge (37). Thus, it is not required in all versions that the thicker jaw necessarily is the jaw that also selectively retains the cartridge. Furthermore, while the present example illustrates jaw (1316), to which placement tip (1619) connects, as a lower jaw relative to jaw (1314), in other versions the thicker jaw having placement tip (1619) is an upper jaw that may or may not also include cartridge (37) as mentioned above. In view of the teachings herein, other ways to configure end effector (1612) with placement tip (1619) on the thicker jaw will be apparent to those of ordinary skill in the art.

Referring again to FIG. 15, FIG. 15 illustrates reference markings that define multiple zones that can be used to describe the location or placement of the end of the placement tip of an exemplary end effector. For instance, a first reference plane (P1) is defined by a top surface of jaw (1316), and second reference plane (P2) is defined by a distal end of jaw (1316). Additionally, a third reference plane (P3) is defined by a bottom surface of jaw (1316). Third reference plane (P3) in the present example is parallel with first reference plane (P1) and also orthogonal to second reference plane (P2). With this configuration, six zones are defined by the intersections of first and third reference planes (P1, P3) with second reference plane (P2).

A first zone (Z1) is the region above the top surface of jaw (1316) (corresponding with first reference plane (P1)) and proximal to the distal end of jaw (1316) (corresponding with second reference plane (P2)). A second zone (Z2) is shown as the region above the top surface of jaw (1316) (corresponding with first reference plane (P1)) and distal to the distal end of jaw (1316) (corresponding with second reference plane (P2)). A third zone (Z3) is shown as the region below the top surface of jaw (1316) (corresponding with first reference plane (P1)) yet above the bottom surface of jaw (1316) (corresponding with third reference plane (P3)), and proximal to the distal end of jaw (1316) (corresponding with second reference plane (P2)). A fourth zone (Z4) is shown as the region below the top surface of jaw (1316) (corresponding with first reference plane (P1)) yet above the bottom surface of jaw (1316) (corresponding with third reference plane (P3)), and distal to the distal end of jaw (1316) (corresponding with second reference plane (P2)). A fifth zone (Z5) is shown as the region below the bottom surface of jaw (1316) (corresponding with third reference plane (P3)), and proximal to the distal end of jaw (1316) (corresponding with second reference plane (P2)). A sixth zone (Z6) is shown as the region below the bottom surface of jaw (1316) (corresponding with third reference plane (P3)), and distal to the distal end of jaw (1316) (corresponding with second reference plane (P2)).

Using this reference system, exemplary end effectors (1312, 1412, 1512, 1612) can be described in a way that illustrates various locations or placements for the end of the various placement tips when the end effector is in a closed and unloaded state. Referring to FIG. 15, the illustrated configuration shows placement tip (1319) extends through third zone (Z3) and fourth zone (Z4), and the location of an end (1320) of placement tip (1319) is in second zone (Z2). In view of the teachings herein, it will be apparent to those of ordinary skill in the art that when placement tip (1319) is deformable and end effector (1312) is in a closed and loaded state that the location of end (1320) of placement tip (1319) may deflect yet remain in second zone (Z2), or placement tip (1319) may deflect such that end (1320) changes its location in the closed and loaded state to another one of the zones.

With respect to FIG. 16 and placement tip (1419), the illustrated configuration shows placement tip (1419) extends through third zone (Z3), fourth zone (Z4), second zone (Z2), and the location of an end (1420) of placement tip (1419) is in first zone (Z1). In view of the teachings herein, it will be apparent to those of ordinary skill in the art that when placement tip (1419) is deformable and end effector (1412) is in a closed and loaded state that the location of end (1420) of placement tip (1419) may deflect yet remain in first zone (Z1), or placement tip (1419) may deflect such that end (1420) changes its location in the closed and loaded state to another one of the zones.

With respect to FIG. 17 and placement tip (1519), the illustrated configuration shows placement tip (1519) extends through third zone (Z3), and the location of an end (1520) of placement tip (1519) is in fourth zone (Z4). In view of the teachings herein, it will be apparent to those of ordinary skill in the art that when placement tip (1519) is deformable and end effector (1512) is in a closed and loaded state that the location of end (1520) of placement tip (1519) may deflect yet remain in fourth zone (Z4), or placement tip (1519) may deflect such that end (1520) changes its location in the closed and loaded state to another one of the zones.

With respect to FIG. 18 and placement tip (1619), the illustrated configuration shows placement tip (1619) extends through third zone (Z3), fourth zone (Z4), and the location of an end (1620) of placement tip (1619) is in second zone (Z2). In view of the teachings herein, it will be apparent to those of ordinary skill in the art that when placement tip (1619) is deformable and end effector (1612) is in a closed and loaded state that the location of end (1620) of placement tip (1619) may deflect yet remain in second zone (Z2), or placement tip (1619) may deflect such that end (1620) changes its location in the closed and loaded state to another one of the zones.

In view of the teachings herein, various ways to configure an end effector to locate an end of a placement tip in a desired position under various conditions, i.e. open/closed and loaded/unloaded, will be apparent to those of ordinary skill in the art. Furthermore, the reference system described above can also be implemented in accordance with at least some of the teachings of U.S. patent application Ser. No. 16/035,856, entitled "Surgical Stapling End Effector Component with Tip Having Varying Bend Angle," filed on Jul. 16, 2018, published as U.S. Pub. No. 2018/0325514 on Nov. 15, 2018, the disclosure of which is incorporated by reference herein. Various suitable ways in which the teachings herein may be combined with the teachings of U.S. patent application Ser. No. 16/035,856 filed on Jul. 16, 2018, published as U.S. Pub. No. 2018/0325514 on Nov. 15, 2018, will be apparent to those of ordinary skill in the art.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprises (a) a body, (b) a shaft extending from the body, wherein the shaft defines a first longitudinal axis, and (c) an end effector in communication with the shaft, wherein the end effector is operable to compress, staple, and cut tissue. The end effector comprises (i) a first jaw, (ii) a second jaw opposing the first jaw, wherein at least one of the jaws is operable to move relative to the other jaw between an open position and a closed position, wherein the first jaw has a greater thickness than the second jaw, wherein the first jaw defines a second longitudinal axis, and (iii) a placement tip extending distally from the first jaw. The placement tip comprises a taper, wherein the placement tip defines a third longitudinal axis that is not parallel with the second longitudinal axis defined by the first jaw from which the placement tip extends. The third longitudinal axis defined by the placement tip extends in a direction towards the second jaw.

Example 2

The apparatus of Example 1, wherein the placement tip is elastically deformable.

Example 3

The apparatus of any one or more of Examples 1 through 2, wherein the placement tip is comprised of a first resilient material, wherein the first jaw from which the placement tip extends is comprised of a second material, and wherein the first resilient material has a lower stiffness than the second material.

Example 4

The apparatus of any one or more of Examples 1 through 3, wherein the placement tip is configured to deflect in response to a clamping force applied to the placement tip.

Example 5

The apparatus of any one or more of Examples 1 through 4, further comprising a cartridge configured to hold one or more staples, wherein the cartridge selectively connects with the first jaw.

Example 6

The apparatus of any one or more of Examples 1 through 5, further comprising an anvil configured to be contacted by the one or more staples of the cartridge, wherein the second jaw comprises the anvil.

Example 7

The apparatus of any one or more of Examples 1 through 6, wherein the anvil is movable relative to the cartridge between the open position and the closed position.

Example 8

The apparatus of any one or more of Examples 1 through 7, wherein the placement tip is configured such that, when the end effector is in a closed and unloaded state, the placement tip contacts a portion of the second jaw, and wherein when the end effector is in a loaded state with tissue between the first and second jaws, the placement tip deflects away from the second jaw.

Example 9

The apparatus of any one or more of Examples 1 through 7, wherein the placement tip extends distally from the first jaw in a straight manner.

Example 10

The apparatus of any one or more of Examples 1 through 8, wherein the placement tip extends distally from the first jaw in a curved manner.

Example 11

The apparatus of any one or more of Examples 1 through 7 and 9 through 10, wherein the end effector is configured such that there is a gap between the placement tip and the second jaw when the end effector is in a closed and unloaded state.

Example 12

The apparatus of any one or more of Examples 1 through 11, wherein the first jaw extends further distally than the second jaw.

Example 13

The apparatus of any one or more of Examples 1 through 12, wherein the first jaw comprises an upper surface, wherein the placement tip extends in a curved manner past the upper surface of the first jaw toward the second jaw.

Example 14

The apparatus of any one or more of Examples 1 through 13, wherein the taper of the placement tip comprises a lateral taper.

Example 15

The apparatus of any one or more of Examples 1 through 14, wherein the taper of the placement tip comprises a longitudinal taper, and the placement tip comprises a pointed distal end.

Example 16

An apparatus, comprises (a) a body, (b) a shaft extending from the body, wherein the shaft defines a first longitudinal axis, and (c) an end effector in communication with the shaft, wherein the end effector is operable to compress, staple, and cut tissue. The end effector comprises (i) a first jaw, (ii) a second jaw opposing the first jaw, wherein at least one of the jaws is movable relative to the other jaw between an open position and a closed position, wherein the first jaw has a greater thickness than the second jaw, wherein the first jaw defines a second longitudinal axis, and (iii) a placement tip comprised of a resilient material, and extending distally from the first jaw. The placement tip defines a third longitudinal axis that is oblique relative to the second longitudinal axis defined by the first jaw from which the placement tip extends. The third longitudinal axis defined by the placement tip extends in a direction towards the second jaw.

Example 17

The apparatus of Example 16, wherein the first jaw is an upper jaw.

Example 18

The apparatus of Example 16, wherein the first jaw is a lower jaw.

Example 19

The apparatus of any one or more of Examples 16 through 18, wherein the placement tip comprises a lower stiffness than the first jaw.

Example 20

An apparatus, comprises (a) a body, (b) a shaft extending from the body, wherein the shaft defines a first longitudinal axis, and (c) an end effector in communication with the shaft, wherein the end effector is operable to compress, staple, and cut tissue. The end effector comprises (i) a first jaw, wherein the first jaw is comprised of a first material, (ii) a second jaw opposing the first jaw, wherein at least one of the jaws is movable relative to the other jaw between an open position and a closed position, wherein the first jaw has a greater thickness than the second jaw, wherein the first jaw defines a second longitudinal axis, and (iii) a placement tip extending distally from the first jaw. The placement tip is comprised of a second material, wherein the second material is resilient, and wherein the placement tip comprises a lower stiffness than the first jaw.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed Feb. 17, 2017, issued as U.S. Pat. No. D836,198 on Dec. 18, 2018, the disclosure of which is incorporated by reference herein. Various suitable ways in which the teachings herein may be combined with the teachings of U.S. patent application Ser. No. 29/594,332, issued as U.S. Pat. No. D836,198 on Dec. 18, 2018, will be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed Feb. 17, 2017, issued as U.S. Pat. No. D833,010 on Nov. 6, 2018, the disclosure of which is incorporated by reference herein. Various suitable ways in which the teachings herein may be combined with the teachings of U.S. patent application Ser. No. 29/594,335, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed Feb. 17, 2017, issued as U.S. Pat. No. 10,729,434 on Aug. 4, 2020, the disclosure of which is incorporated by reference herein. Various suitable ways in which the teachings herein may be combined with the teachings of U.S. patent application Ser. No. 15/435,607, issued as U.S. Pat. No. 10,729,434 on Aug. 4, 2020, will be apparent to those of ordinary skill in the art.

It should also be understood that the teachings herein may be readily combined with various teachings in U.S. patent application Ser. No. 15/435,618, entitled "Surgical Stapler with Cooperating Distal Tip Features on Anvil and Staple Cartridge," filed Feb. 17, 2017, issued as U.S. Pat. No. 10,806,451 on Oct. 20, 2020, the disclosure of which is incorporated by reference herein. Various suitable ways in which the teachings herein may be combined with the teachings of U.S. patent application Ser. No. 15/435,618, issued as U.S. Pat. No. 10,806,451 on Oct. 20, 2020, will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed Feb. 17, 2017, issued as U.S. Pat. No. D836,199 on Dec. 18, 2018, the disclosure of which is incorporated by reference herein. Various suitable ways in which the teachings herein may be combined with the teachings of U.S. patent application Ser. No. 29/594,340, issued as U.S. Pat. No. D836,199 on Dec. 18, 2018, will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed Feb. 17, 2017, issued as U.S. Pat. No. 10,758,231 on Sep. 1, 2020, the disclosure of which is incorporated by reference herein. Various suitable ways in which the teachings herein may be combined with the teachings of U.S. patent application Ser. No. 15/435,631, issued as U.S. Pat. No. 10,758,231 on Sep. 1, 2020, will be apparent to those of ordinary skill in the art.

It should also be understood that the teachings herein may be readily combined with various teachings in U.S. patent application Ser. No. 16/035,856, entitled "Surgical Stapling End Effector Component with Tip Having Varying Bend Angle," filed on Jul. 16, 2018, published as U.S. Pub. No. 2018/0325514 on Nov. 15, 2018, the disclosure of which is incorporated by reference herein. Various suitable ways in which the teachings herein may be combined with the teachings of U.S. Patent application Ser. No. 16/035,856, filed on Jul. 16, 2018, published as U.S. Pub. No. 2018/0325514 on Nov. 15, 2018, will be apparent to those of ordinary skill in the art.

It should also be understood that the teachings herein may be readily combined with various teachings in U.S. patent application Ser. No. 16/035,865, entitled "Method of Surgical Stapling with End Effector Component Having a Curved Tip," filed on Jul. 16, 2018, published as U.S. Pub. No. 2018/0325516 on Nov. 15, 2018, the disclosure of which is incorporated by reference herein. Various suitable ways in which the teachings herein may be combined with the teachings of U.S. patent application Ser. No. 16/035,865 filed on Jul. 16, 2018, published as U.S. Pub. No. 2018/0325516 on Nov. 15, 2018, will be apparent to those of ordinary skill in the art.

It should also be understood that the teachings herein may be readily combined with various teachings in U.S. patent application Ser. No. 16/035,872, entitled "Permanent Attachment Means for Curved Tip of Component of Surgical Stapling Instrument," filed on Jul. 16, 2018, issued as U.S. Pat. No. 10,973,515 on Apr. 13, 2021, the disclosure of which is incorporated by reference herein. Various suitable ways in which the teachings herein may be combined with the teachings of U.S. patent application Ser. No. 16/035,872 filed on Jul. 16, 2018, issued as U.S. Pat. No. 10,973,515 on Apr. 13, 2021, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System, issued Sep. 30, 2014, the disclosure of which is incorporated by reference herein; U.S. Pat. No. 8,820,605, entitled "Robotically-Controlled Surgical Instrument with Force-Feedback Capabilities," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector Systems with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
 (a) a body;
 (b) a shaft extending from the body, wherein the shaft defines a first longitudinal axis; and

(c) an end effector in communication with the shaft, wherein the end effector is operable to compress, staple, and cut tissue, wherein the end effector comprises:
   (i) a first jaw,
   (ii) a second jaw opposing the first jaw, wherein at least one of the jaws is movable relative to the other jaw between an open position and a closed position, wherein the first jaw has a greater thickness than the second jaw, wherein the first jaw defines a second longitudinal axis, and
   (iii) a placement tip comprised of a resilient material, wherein the placement tip comprises a lower lip attached with an angled distal surface of the first jaw, and an upper lip extending in a direction towards the second jaw, wherein the upper lip extends from and connects with a proximal portion of the lower lip with a distal portion of the upper lip disconnected from the lower lip, wherein the upper lip and the lower lip define a space therebetween.

2. The apparatus of claim 1, wherein the first jaw is an upper jaw.

3. The apparatus of claim 1, wherein the first jaw is a lower jaw.

4. The apparatus of claim 1, wherein the placement tip comprises a lower stiffness than the first jaw.

5. The apparatus of claim 1, wherein the placement tip is configured to reduce drag when maneuvering the end effector when in a closed and unloaded state by contacting a portion of the second jaw to fill a gap between the first jaw and the second jaw when the end effector is in the closed and unloaded state.

6. The apparatus of claim 1, wherein the placement tip comprises tissue gripping features.

7. The apparatus of claim 6, wherein the tissue gripping features are located on a top surface of the upper lip.

8. The apparatus of claim 1, wherein the placement tip comprises a divider extending from the lower lip and connecting the lower lip with the upper lip.

9. The apparatus of claim 8, wherein the placement tip comprises two dividers.

10. The apparatus of claim 1, wherein the placement tip comprises a void space between the upper lip and the lower lip.

11. An apparatus, comprising:
(a) a body;
(b) a shaft extending from the body, wherein the shaft defines a first longitudinal axis; and
(c) an end effector in communication with the shaft, wherein the end effector is operable to compress, staple, and cut tissue, wherein the end effector comprises:
   (i) a first jaw,
   (ii) a second jaw opposing the first jaw, wherein at least one of the jaws is movable relative to the other jaw between an open position and a closed position, wherein the first jaw has a greater thickness than the second jaw, wherein the first jaw defines a second longitudinal axis, and
   (iii) a placement tip comprised of a resilient material, wherein the placement tip comprises a lower lip attached with an angled distal surface of the first jaw, and an upper lip extending in a direction towards the second jaw, wherein the placement tip comprises a void space between the upper lip and the lower lip.

12. The apparatus of claim 11, wherein the placement tip comprises a divider extending within the void space from the lower lip and connecting the lower lip with the upper lip.

13. The apparatus of claim 12, wherein the placement tip comprises two dividers.

14. An apparatus, comprising:
(a) a body;
(b) a shaft extending from the body, wherein the shaft defines a first longitudinal axis; and
(c) an end effector in communication with the shaft, wherein the end effector is operable to compress, staple, and cut tissue, wherein the end effector comprises:
   (i) a first jaw,
   (ii) a second jaw opposing the first jaw, wherein at least one of the jaws is movable relative to the other jaw between an open position and a closed position, wherein the first jaw has a greater thickness than the second jaw, wherein the first jaw defines a second longitudinal axis, and
   (iii) a placement tip comprised of a resilient material, wherein the placement tip comprises a lower lip attached with an angled distal surface of the first jaw, an upper lip extending in a direction towards the second jaw, and two or more dividers extending from the lower lip and connecting the lower lip with the upper lip.

* * * * *